United States Patent [19]

Blum

[11] 4,136,283

[45] Jan. 23, 1979

[54] TOMOGRAPHIC APPARATUS AND METHOD

[76] Inventor: Alvin S. Blum, 2350 Del Mar Place, Fort Lauderdale, Fla. 33301

[21] Appl. No.: 854,896

[22] Filed: Nov. 25, 1977

Related U.S. Application Data

[63] Continuation of Ser. No. 380,203, Jul. 18, 1973, abandoned, and a continuation of Ser. No. 650,321, Jan. 19, 1976, abandoned.

[51] Int. Cl.$^2$ .............................................. G01T 1/20
[52] U.S. Cl. ................................. 250/363 S; 250/505
[58] Field of Search ............... 250/505, 445 T, 363 S, 250/361, 508, 313

[56] References Cited

U.S. PATENT DOCUMENTS

| | | | |
|---|---|---|---|
| 3,499,146 | 3/1910 | Richards | 250/445 T |
| 3,714,429 | 1/1973 | McAfee et al. | 250/445 T |
| 3,778,614 | 12/1973 | Houndsfield et al. | 250/445 T |
| 3,784,820 | 1/1974 | Miraldi | 250/445 T |

Primary Examiner—Alfred E. Smith
Assistant Examiner—B. C. Anderson

Attorney, Agent, or Firm—Malin & Haley

[57] ABSTRACT

The present invention relates to a new and improved tomographic visualization apparatus and method. The apparatus includes a camera with a stationary collimator of a radiation dense material with channels therein for collecting radiation from a body which passes through the channels in the collimator. The radiation is thereafter detected and the signal information is processed so as to provide images of selected depths within the body. The stationary collimator includes a plurality of matching sections wherein, the center lines of the holes or channels in each sector are parallel to each other and the angular position of their center lines are at a sloping angle in relation to the surface plane of the scintillation crystal of the camera. The center lines of the channels in one sector are not parallel to the center lines of those of any other sector but slope toward the common plane of intersection along the camera axis to provide matching tomographic collimator sections. The images from the collimator sections are superimposed over one another in varying degrees to provide the reinforced images at varying depths.

3 Claims, 4 Drawing Figures

4,136,283

TOMOGRAPHIC APPARATUS AND METHOD

BACKGROUND OF THE INVENTION

This is a continuation of application Ser. No. 380,203, filed July 18, 1973 abandoned and application Ser. No. 650,321 filed Jan. 19, 1976 abandoned.

This invention is related to a plurality of matching tomographic collimator sections for providing reinforced image information simultaneously at particular planes when imaging radiation comes from a body without physically moving the camera or the body.

Tomography enhances the radiation image in one plane of the radiating body while details of adjoining planes are blurred. Typical prior art embodiments involve a multi-channeled, inclined hole collimator, with all holes parallel, that is moved parallel to the plane of observation, see McAfee, J. G. et al; longitudinal Tomographic Radioisotopic Imaging with a Scintillation Camera: Theoretical Considerations of a New Method; Journal of Nuclear Medicine, page 654, October, 1969. Other devices have moved the object or body being viewed rather than moving the observing device or camera see Cooke, Michael B. D. et al; Whole-Body Imaging and Count Profiling with a Modified Anger Camera II. Implementation Evaluation page 903, Vol. 13, No. 12; Journal of Nuclear Medicine. The final image produced by the device or body moving equipment may be distorted. Also, moving the observation device may interfere with the accurate recordation of rapidly changing events taking place in the body being observed. Further, the H. O. Anger U.S. Pat. Nos. 3,011,057 and 3,432,660 show that the use of a camera and an electronic display means are old. Further, Alvin S. Blum's copending patent application Ser. No. 158,503 filed June 30, 1971 shows an image detecting and processing means and a display means.

BRIEF DESCRIPTION OF THE INVENTION

The present invention relates to a new and improved tomographic visualization apparatus and method. The apparatus includes a scintillation camera with a stationary plural sectioned collimator for collecting data, a display processor, a superimposition means, and a display means to provide reinforced images at a plurality of depths within the viewed body. The stationary collimator collects radiation from a body which passes through channels in the collimator. The radiation is thereafter detected and the signal information is processed so as to provide images of selected depths within the body. The stationary collimator, a radiation dense material with holes or channels, includes a plurality of matching sections wherein, the center lines of the holes or channels in each sector are parallel to each other. The center lines of one sector are not parallel to the center lines of those of any other sector. The angular position of the center lines are at a sloping angle in relation to the surface plane of the scintillation crystal. The center line of each hole slopes toward the common plane of intersection of each section along the camera axis to provide common reading plane areas. The collimator consists of at least two sections with each section having holes that slope in relation to the surface plane of the scintillation crystal to provide matching tomographic collimator sections. The sections may provide one maximum common reading plane area that represents a particular plane of depth in the body being viewed. The sections also provide adjacent common reading plane areas that represent other planes of depth in the body on either side of the maximum common reading plane area.

All the collimator sections provide data that may be readily superimposed to provide reinforced images, each at a particular depth within the irradiating body. The image data from each section is superimposed by degree over the other collimator section data to provide the reinforced images at various depths. Superimposition may be accomplished by electronics means or photographic means simultaneously or sequentially. In a collimator having two sections the image may also be read stereoscopically by a human operator without providing separate electronic or photographic superimposition means. The human brain performs the multiple depth visualization of the image simultaneously.

It is an object of this invention to provide a non-complex means whereby radiation events may be observed tomographically with no parts moving during the observation of the event.

It is a further object of this invention to increase the sensitivity of the overall system by observing an event through more than one set of holes in the collimator.

Another object is to provide a plurality of sections of a collimator wherein each section has matching parallel holes that are directed toward a maximum common plane to provide depth information.

In accordance with these and other objects of this invention which will become apparent hereinafter, the instant invention will now be described with particular reference to the accompanying drawings.

DESCRIPTION OF ONE PREFERRED EMBODIMENT

Figure 1:
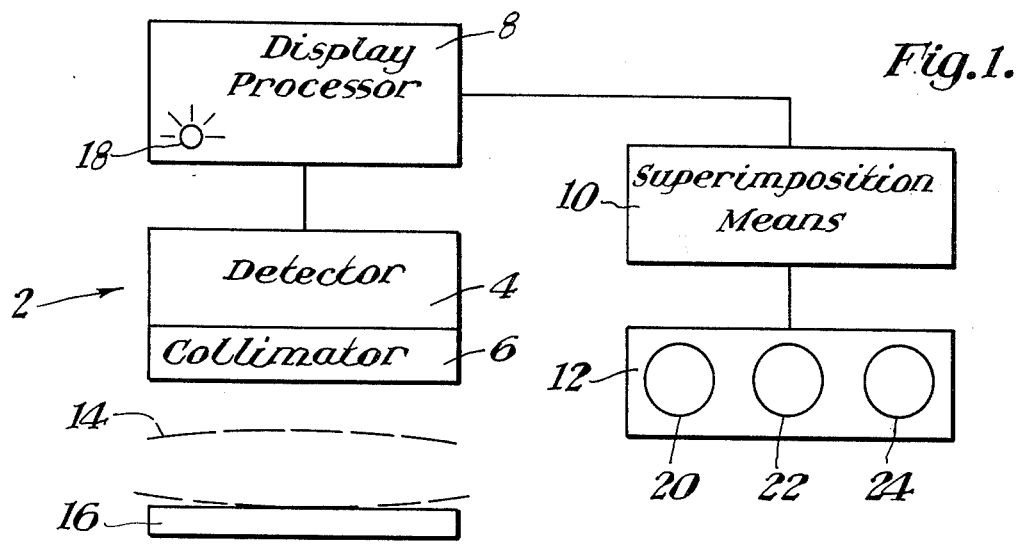
FIG. 1 is a block diagram of the tomograhic device.

Referring now in detail to FIG. 1, illustrating the tomograhic visualization device, the device, generally designated by numeral 2, includes a detector 4, with a collimator 6, connected to an image data processor 8, that is connected to a superimposition means 10 that is connected to a display means 12. The patient or body 14 represented in dotted lines is positioned on the fixed platform or table 16. The detector 4 is operated in a similar manner to the Anger camera to provide data from radiation from the body. The display processor 8 may be constructed similar to the Anger devices or the type of system disclosed in the prior Blum Patent Application, in order to accumulate and store radiation emission data for recall in order to provide an output display representing the event taking place within the body. Any well known electronic means 10 together with the sectioned collimator data may provide reinforced images at particular depths within the radiating body on display means 12 without relative movement of the detector 4, collimator 6, the table 16, or the body 14 during the event. The display processor includes an actuating dial 18, the operation of which is set forth herebelow. The display means 12 may include video tubes 20, 22, 24 for presenting planes y and z respectively.

Figure 2:
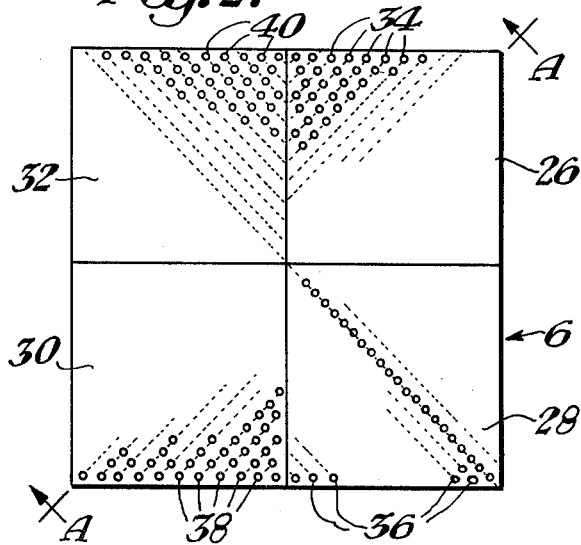
FIG. 2 is a top plan view of the collimator.
Figure 3:
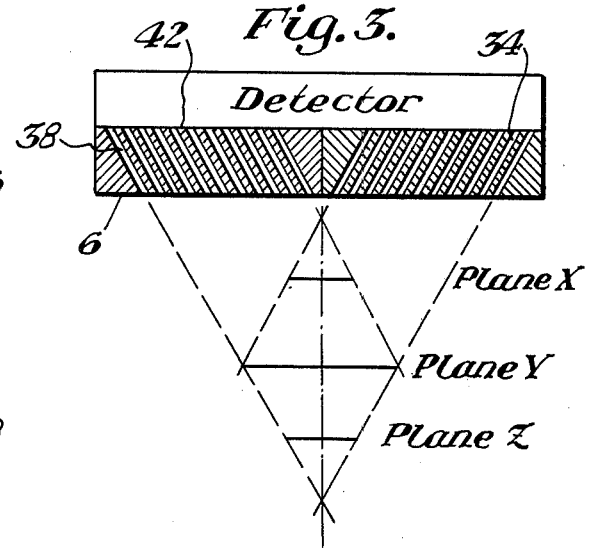
FIG. 3 is a cross-sectional view of FIG. 2 taken along line A—A and looking in the direction of the arrows illustrating the common planes.
Figure 4:
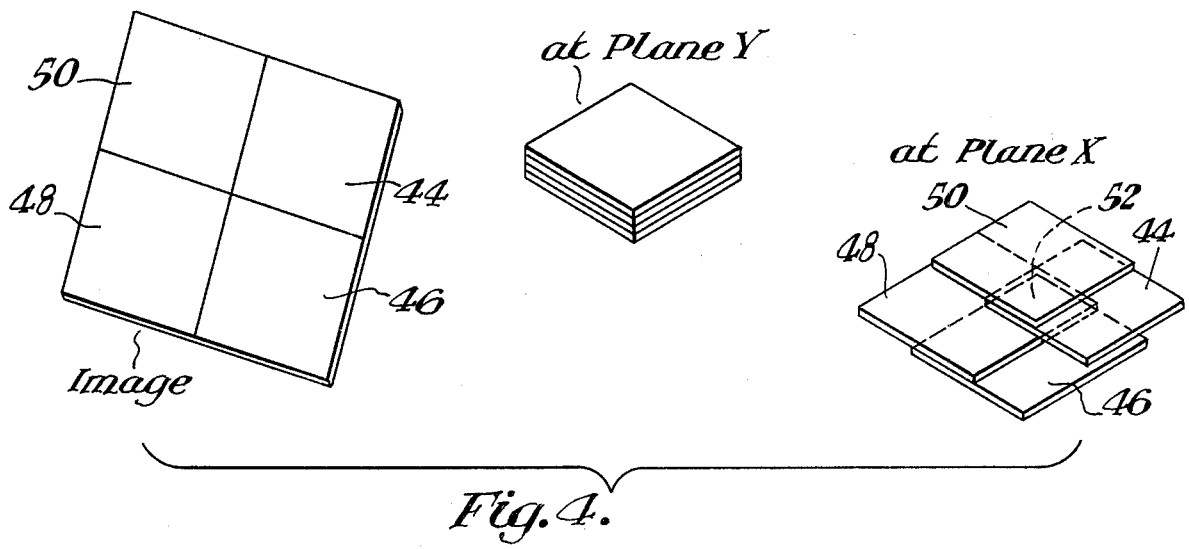
FIG. 4 is an exploded view of the image with four matching sections from the collimator, illustrating two different superimposed positions for reinforcing the image at particular depths at plane x and y.

Referring now to FIGS. 2, 3 and 4 the stationary collimator 6 includes a plurality of matching sections 26, 28, 30 and 32 wherein, the center lines of the holes or channels 34 or 36 or 38 or 40 in each sector are parallel to each other. The center lines of the channels of one sector are not parallel to center lines of channels of an adjacent sector. The angular position of the center lines of all channels slope at an angle in relation to the surface plane of the camera face 42 or the scintillation crystal in the detector 4. The center lines slope toward the common plane y of intersection along the camera axis. The collimator 6, shown in FIG. 2, consists of four sections 26, 28, 30 and 32 with each section having holes 34, 36, 38 and 40 respectively that slope in relation to the surface plane of the scintillation crystal. The sections provide one maximum common reading plane area, plane y, that represents a plane of depth in the radiating body 14 or a distance from the detector 4. The sections also provide adjacent common reading plane areas, planes x and z that represent other planes of various depths in the radiation body.

The collimator 6 provides a plurality of generally matching image data that is viewed by the detector 4 for storage in the data processor 8. The data processor 8 can display the image data in a video tube 20, 22 and 24. The four images 44, 46, 48 and 50 illustrated in FIG. 4 may be superimposed optically by well known means or electronically as shown in FIG. 1 by well known means to provide a reinforced image of the maximum common reading plane area at plane y at a particular depth within the body 14 by full superimposition of each image sector of each section. A partial or degree of superimposition of each image sector 44, 46, 48 and 50 of each section at plane x is illustrated by reinforced image, shown by dotted lines 52.

In use, the camera views the radiation from the body from a plurality of positions or areas. The areas are the sections of the collimator. The collimator collimates the random radiation traveling from the body toward the camera. By collimating the traveling radiation from the body, a plurality of beams of generally parallel rays are produced on the opposite side of the collimator. The radiation is collimated in such a manner that the projections of each beam intersect within the body being viewed. Thereafter, the camera and the display processing means provides an image from each radiation beam. The superimposition means and the display means allow the plurality of images to be superimposed at various degrees to provide a reinforced image at various depths in the body. Reinforced images at planes x, y and z may be displayed simultaneously in video tubes 20, 22 and 24.

The instant invention has been shown and described herein in what is considered to be the most practical and preferred embodiment. It is recognized, however, that departures may be made therefrom within the scope of the invention and that obvious modifications will occur to a person skilled in the art.

What I Claim Is:

1. A tomographic visualization device comprising:
   a data processor means for providing accumulated information,
   a scintillation camera connected to said data processor for providing image data of radiation from a body to said data processor means, said camera including a detector connected to said data processor and a stationary collimator connected to said detector,
   said stationary collimator for collecting data from said body to provide tomographic data including,
   at least two sections each including a large number of channels, said channels in each section having longitudinal center lines generally parallel to each other; and all said channels of at least two sections of said collimator having longitudinal center lines at the same general angle in relation to a single reference plane for at least two sections of said collimator; said longitudinal center lines of the channels in each section intersect the longitudinal center lines of the channels of at least one other section at a large number of planes to reinforce the image at different distances from said stationary collimator,
   said camera and said body fixed in relation to one another during radiation image data collection.

2. A tomographic visualization device as set forth in claim 1 including,
   a superimposition means connected to said camera to provide varying degrees of superimposition of data from each said section to provide reinforced data at particular depths in said body positioned from the camera.

3. A method of providing reinforced images from a radiating body at a particular depth within said body by the steps of,
   simultaneously viewing radiation from a body from a plurality of positions,
   collimating the viewed radiation from each of said positions to provide a plurality of generally parallel beams of radiation,
   collecting images provided by each of the collimated beams, and
   superimposing a plurality of said images one upon the other to provide at least one reinforced image from a particular depth within the body.

* * * * *